(12) United States Patent
Shireman

(10) Patent No.: US 8,002,715 B2
(45) Date of Patent: Aug. 23, 2011

(54) MEDICAL DEVICE INCLUDING A POLYMER SLEEVE AND A COIL WOUND INTO THE POLYMER SLEEVE

(75) Inventor: Brice L. Shireman, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 94 days.

(21) Appl. No.: 12/130,900

(22) Filed: May 30, 2008

(65) Prior Publication Data

US 2009/0299332 A1 Dec. 3, 2009

(51) Int. Cl.
*A61M 25/00* (2006.01)

(52) U.S. Cl. .................................................. 600/585

(58) Field of Classification Search .................. 600/433, 600/434, 585; 604/164.13
See application file for complete search history.

(56) References Cited

U.S. PATENT DOCUMENTS

| | | | |
|---|---|---|---|
| 4,456,017 A | 6/1984 | Miles | |
| 4,764,324 A | 8/1988 | Burnham | |
| 4,922,924 A | 5/1990 | Gambale et al. | |
| 4,934,380 A | 6/1990 | De Toledo | |
| 5,095,915 A | 3/1992 | Engelson | |
| 5,129,890 A * | 7/1992 | Bates et al. | 604/529 |
| 5,147,317 A | 9/1992 | Shank et al. | |
| 5,174,295 A | 12/1992 | Christian et al. | |
| 5,238,004 A | 8/1993 | Sahatjian et al. | |
| 5,244,619 A | 9/1993 | Burnham | |
| 5,251,640 A | 10/1993 | Osborne | |
| 5,333,620 A | 8/1994 | Moutafis et al. | |
| 5,358,493 A | 10/1994 | Schweich, Jr. et al. | |
| 5,406,960 A | 4/1995 | Corso, Jr. | |
| 5,433,200 A | 7/1995 | Fleischhacker, Jr. | |
| 5,437,288 A | 8/1995 | Schwartz et al. | |
| 5,452,726 A | 9/1995 | Burmeister et al. | |
| 5,456,732 A | 10/1995 | Baxter | |
| 5,497,785 A | 3/1996 | Viera | |
| 5,549,580 A * | 8/1996 | Diaz | 604/523 |
| 5,551,443 A | 9/1996 | Sepetka et al. | |
| 5,599,492 A | 2/1997 | Engelson | |
| 5,636,642 A | 6/1997 | Palermo | |

(Continued)

FOREIGN PATENT DOCUMENTS

DE 10138953 2/2003

(Continued)

*Primary Examiner* — Max Hindenburg
*Assistant Examiner* — Jonathan M Foreman
(74) *Attorney, Agent, or Firm* — Seager, Tufte & Wickhem, LLC

(57) ABSTRACT

Medical devices and methods for making and using the same. An example medical device may include an elongate core member having a proximal portion and a distal portion. A polymer jacket may be disposed about at least a portion of the core member. The jacket may include an outer surface. A lubricious coating may be disposed on the outer surface of the jacket. A coil may be disposed about at least a portion of the jacket. The coil may have an outer surface and may include a first section and a second section. At least a portion of the outer surface of the coil along the first section may be flush with or recessed below the outer surface of the polymer jacket. At least a portion of the outer surface of the coil along the second section may protrude from the outer surface of the polymer jacket, may be free of the coating, and may define a region of decreased lubricity.

19 Claims, 6 Drawing Sheets

U.S. PATENT DOCUMENTS

| | | | |
|---|---|---|---|
| 5,666,969 | A | 9/1997 | Urick et al. |
| 5,722,424 | A | 3/1998 | Engelson |
| 5,749,837 | A | 5/1998 | Palermo et al. |
| 5,769,796 | A | 6/1998 | Palermo et al. |
| 5,772,609 | A | 6/1998 | Nguyen et al. |
| 5,827,201 | A | 10/1998 | Samson et al. |
| 5,830,155 | A | 11/1998 | Frechette et al. |
| 5,836,893 | A | 11/1998 | Urick |
| 5,840,046 | A | 11/1998 | Deem |
| 5,876,356 | A | 3/1999 | Viera et al. |
| 5,885,227 | A | 3/1999 | Finlayson |
| 5,897,819 | A | 4/1999 | Miyata et al. |
| 5,910,364 | A | 6/1999 | Miyata et al. |
| 5,951,494 | A | 9/1999 | Wang et al. |
| 5,984,877 | A | 11/1999 | Fleischhacker, Jr. |
| 5,984,878 | A | 11/1999 | Engelson |
| 6,017,335 | A | 1/2000 | Burnham |
| 6,019,736 | A | 2/2000 | Avellanet et al. |
| 6,042,876 | A | 3/2000 | Deem |
| 6,056,702 | A | 5/2000 | Lorenzo |
| 6,059,738 | A | 5/2000 | Stoltze et al. |
| 6,096,068 | A | 8/2000 | Dobak et al. |
| 6,106,485 | A | 8/2000 | McMahon |
| 6,107,004 | A | 8/2000 | Donadio, III |
| 6,139,510 | A | 10/2000 | Palermo |
| 6,168,571 | B1 | 1/2001 | Solar et al. |
| 6,245,030 | B1 | 6/2001 | DuBois et al. |
| 6,245,095 | B1 | 6/2001 | Dobak, III et al. |
| 6,251,085 | B1 | 6/2001 | Tezuka |
| 6,251,086 | B1 | 6/2001 | Cornelius et al. |
| 6,254,550 | B1 | 7/2001 | McNamara et al. |
| 6,296,616 | B1 | 10/2001 | McMahon |
| 6,306,105 | B1 * | 10/2001 | Rooney et al. ............... 600/585 |
| 6,340,441 | B1 | 1/2002 | Meyer et al. |
| 6,390,992 | B1 | 5/2002 | Morris et al. |
| 6,402,706 | B2 | 6/2002 | Richardson et al. |
| 6,409,682 | B1 | 6/2002 | Burmeister et al. |
| 6,409,683 | B1 | 6/2002 | Fonseca et al. |
| 6,436,056 | B1 | 8/2002 | Wang et al. |
| 6,461,311 | B2 | 10/2002 | DuBois et al. |
| 6,488,637 | B1 | 12/2002 | Eder et al. |
| 6,494,847 | B1 | 12/2002 | Richardson et al. |
| 6,494,894 | B2 | 12/2002 | Mirarchi |
| 6,496,894 | B1 | 12/2002 | Fanning |
| 6,508,803 | B1 | 1/2003 | Horikawa et al. |
| 6,544,197 | B2 | 4/2003 | DeMello |
| 6,602,207 | B1 | 8/2003 | Mam et al. |
| 6,918,882 | B2 | 7/2005 | Skujins et al. |
| 7,070,605 | B2 | 7/2006 | Katsumoto et al. |
| 7,071,197 | B2 | 7/2006 | Leonardi et al. |
| 7,074,197 | B2 | 7/2006 | Reynolds et al. |
| 7,553,287 | B2 | 6/2009 | Reynolds et al. |
| 2002/0038131 | A1 | 3/2002 | Burmeister et al. |
| 2004/0143239 | A1 | 7/2004 | Zhou et al. |
| 2004/0167436 | A1 | 8/2004 | Reynolds et al. |
| 2004/0167438 | A1 | 8/2004 | Sharrow |
| 2004/0167441 | A1 | 8/2004 | Reynolds et al. |
| 2005/0075582 | A1 | 4/2005 | Cornelius et al. |
| 2005/0096567 | A1 * | 5/2005 | Reynolds et al. ............... 600/585 |
| 2005/0096665 | A1 | 5/2005 | Reynolds et al. |
| 2006/0122537 | A1 | 6/2006 | Reynolds et al. |
| 2006/0282016 | A1 * | 12/2006 | Cornelius et al. ............... 600/585 |
| 2008/0312597 | A1 | 12/2008 | Uihlein |
| 2010/0069794 | A1 | 3/2010 | Uihlein |

FOREIGN PATENT DOCUMENTS

| | | |
|---|---|---|
| DE | 102006047675 | 4/2008 |
| EP | 0652026 | 5/1995 |
| EP | 0714315 | 5/2002 |
| EP | 0720838 | 3/2003 |
| JP | 2000-107296 | 4/2000 |
| JP | 2007509713 | 4/2007 |
| WO | 8804940 | 7/1988 |
| WO | 9839049 | 9/1998 |
| WO | 9842399 | 10/1998 |
| WO | 03072179 | 9/2003 |
| WO | 2004075726 | 9/2004 |
| WO | 2005002457 | 1/2005 |
| WO | 2005044358 | 5/2005 |
| WO | 2005044360 | 5/2005 |

* cited by examiner

MEDICAL DEVICE INCLUDING A POLYMER SLEEVE AND A COIL WOUND INTO THE POLYMER SLEEVE

FIELD OF THE INVENTION

The present invention pertains to medical devices, and methods for manufacturing medical devices. More particularly, the present invention pertains to guidewires, catheters, and the like as well as methods for manufacturing and using such devices.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

The invention provides design, material, manufacturing method, and use alternatives for medical devices. An example medical device may include an elongate core member having a proximal portion and a distal portion. A polymer jacket may be disposed about at least a portion of the core member. The jacket may include an outer surface. A lubricious coating may be disposed on the outer surface of the jacket. A coil may be disposed about at least a portion of the jacket. The coil may have an outer surface and may include a first section and a second section. At least a portion of the outer surface of the coil along the first section may be flush with or recessed below the outer surface of the polymer jacket. At least a portion of the outer surface of the coil along the second section may protrude from the outer surface of the polymer jacket, may be free of the coating, and may define a region of decreased lubricity.

Another example medical device may include an elongate core member having a proximal portion and a distal portion. A polymer jacket may be disposed on the distal portion. A coil may be disposed on the jacket. The coil may include a first section having a first outer diameter and a second section having a second outer diameter different from the first outer diameter. The first section may be embedded within the jacket. A lubricious coating may be disposed on the jacket. The second section of the coil may be free of the coating and define a region of decreased lubricity.

Another example medical device may include an elongate core member, a polymer jacket disposed on the core member, the jacket having an end, such as a distal or proximal end, and a portion of the core member may extend beyond the end of the jacket. The device may include a coil having a first portion embedded in the jacket, and a second portion extending beyond the end of the jacket. A coating may be disposed on the jacket, and a tip member may be coupled to a distal portion of the jacket and/or a distal portion of the coil and/or a distal portion of the core.

Some other embodiments may relate to methods of making a medical device, such as a guidewire, or the like. One example method may include providing a core wire, disposing a polymer jacket on at least a portion of the core wire, disposing a coil on the jacket, and applying a coating to the jacket. The polymer jacket may have an outer surface. The coil may include a first section and a second section and an outer surface. The coil may be disposed on the jacket such that at least a portion of the outer surface of the coil along the first section is flush with or recessed below the outer surface of the polymer jacket and at least a portion of the outer surface of the coil along the second section protrudes from the outer surface of the polymer jacket. Along the first section of the coil, the coating may adhere to the jacket. Along the second section of the coil, the coil may be free of the coating and may define a region of decreased lubricity.

Another example method may include providing a core wire, disposing a polymer jacket on at least a portion of the core wire, disposing a coil on the jacket, and removing a portion of the polymer jacket such that the coil extends beyond the jacket.

An example guidewire may include an elongate core member having a proximal portion and a distal portion. A polymer jacket may be disposed on the distal portion. A coil may be disposed about at least a portion of the jacket. The coil may have an outer surface and may include a first section and a second section. The outer surface of the coil along the first section may be flush with or recessed below the outer surface of the polymer jacket. The outer surface of the coil along the second section may protrude from the outer surface of the polymer jacket. A lubricous coating may be disposed on the jacket. The coating may define one or more regions of increased lubricity. The second section of the coil may be free of the coating. One or more regions of decreased lubricity may be defined along the second section of the coil.

The above summary of some embodiments is not intended to describe each disclosed embodiment or every implementation of the present invention. The Figures, and Detailed Description, which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
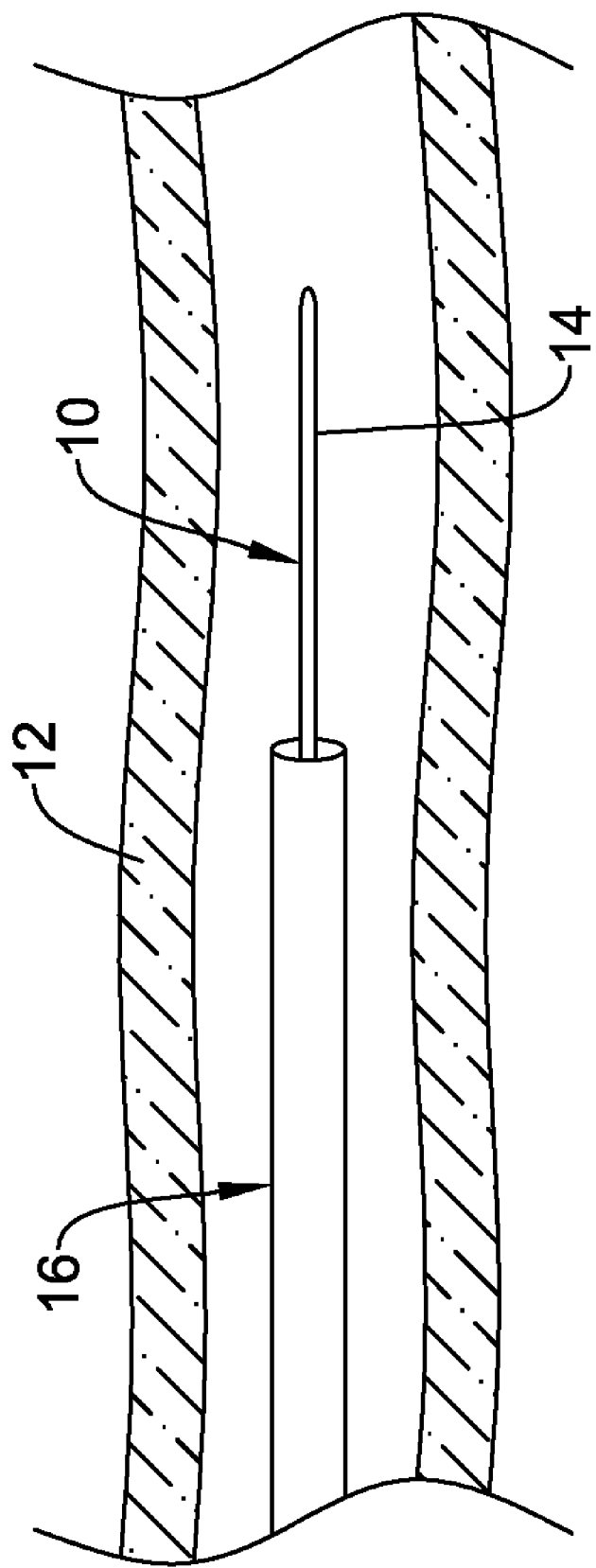
FIG. 1 is a plan view of an example medical device disposed in a blood vessel.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

FIG. 1 is a plan view of an example medical guidewire 10, for example a guidewire, disposed in a blood vessel 12. Guidewire 10 may include a distal section 14 that may be generally configured for probing within the anatomy of a patient. Guidewire 10 may be used for intravascular procedures. For example, guidewire 10 may be used in conjunction with another medical device 16, which may take the form of a catheter, to treat and/or diagnose a medical condition. Of course, numerous other uses are known amongst clinicians for guidewires, catheters, and other similarly configured medical devices.

Although medical guidewire 10 is depicted in the drawings as a guidewire, it is not intended to be limited to just being a guidewire. Indeed, medical guidewire 10 may take the form of any suitable guiding, diagnosing, or treating device (including catheters, endoscopic instruments, laparoscopic instruments, etc., and the like) and it may be suitable for use at essentially any location and/or body lumen within a patient. For example, medical device/guidewire 10 may be suitable for use in neurological interventions, coronary interventions, peripheral interventions, etc. As such, guidewire 10 may be appropriately sized for any given intervention. For example, guidewire 10 may have an outside diameter of about 0.001 to 0.5 inches or about 0.0015 to 0.05 inches for neurological interventions; an outside diameter of about 0.001 to 0.5 inches or about 0.01 to 0.05 inches for coronary interventions; or an outside diameter of about 0.001 to 0.5 inches or about 0.02 to 0.05 inches for peripheral interventions. These dimensions, of course, may vary depending on, for example, the type of device (e.g., catheter, guidewire, etc.), the anatomy of the patient, and/or the goal of the intervention. In at least some embodiments, for example, guidewire 10 may be a crossing guidewire that can be used to help a clinician cross an occlusion or stenosis in vessel 12.

Figure 2:
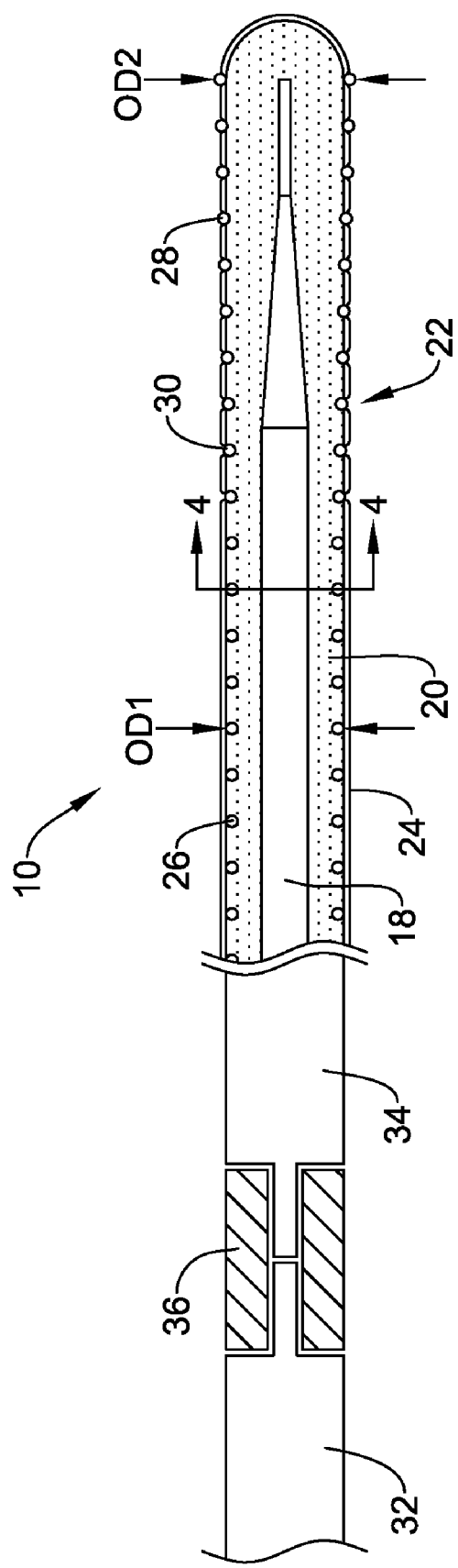
FIG. 2 is a partial cross-sectional view of an example medical device.

Guidewire 10 is illustrated in cross-section in FIG. 2. Here it can be seen that guidewire 10 may include a core wire or core member 18. A polymer jacket 20 may be disposed on or over core wire 18. A coil 22 may be disposed on or over jacket 20. A coating 24 may be disposed over core 18, jacket 20, coil 22, or any combination thereof. In at least some embodiments, coating 24 may include a lubricious material. Some further discussion regarding lubricious materials as well as materials that may be utilized for the various structures of guidewire 10 can be found below.

Coil 22 may have a first section 26 and a second section 28. First section 26 may be wound so as to define a first outer diameter OD1. Second section 28 may be wound so as to define a second outer diameter OD2. The outer diameter of coil 22 may be understood to be the diameter measured of any example cross-section of the generally cylindrical structure defined by coil 22 when it is wound about jacket 20 (and/or any other suitable structure of guidewire 10). The outer diameter may be measured at the outer surface of coil 22 at any portion of coil 22.

Figure 3:
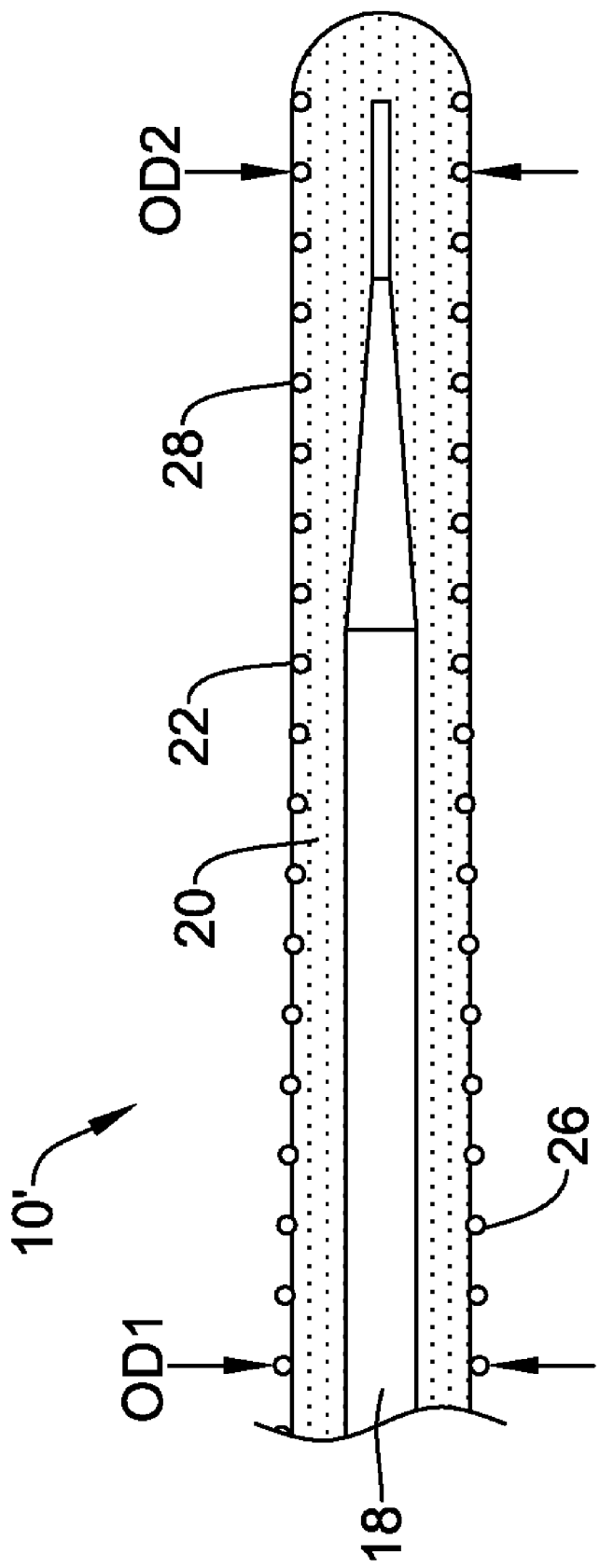
FIG. 3 is a partial cross-sectional view of another example medical device.

Generally, first outer diameter OD1 is different from second outer diameter OD2. For example, first outer diameter OD1 may be smaller than second outer diameter OD2 as depicted in FIG. 2. However, the reverse may also be true. For example, FIG. 3 illustrates guidewire 10' where OD1 is larger than OD2. Coil 22 may also include a transition section 30 where coil transitions from first outer diameter OD1 to second outer diameter OD2. In some embodiments, transition section 30 is relatively short in length so that the transition in outer diameters is relatively abrupt. In other embodiments, however, transition section 30 may be relatively long so as to make the transition in outer diameters relatively gradual. Other lengths between short and long, of course, are also contemplated for transition section 30.

Figure 3A:
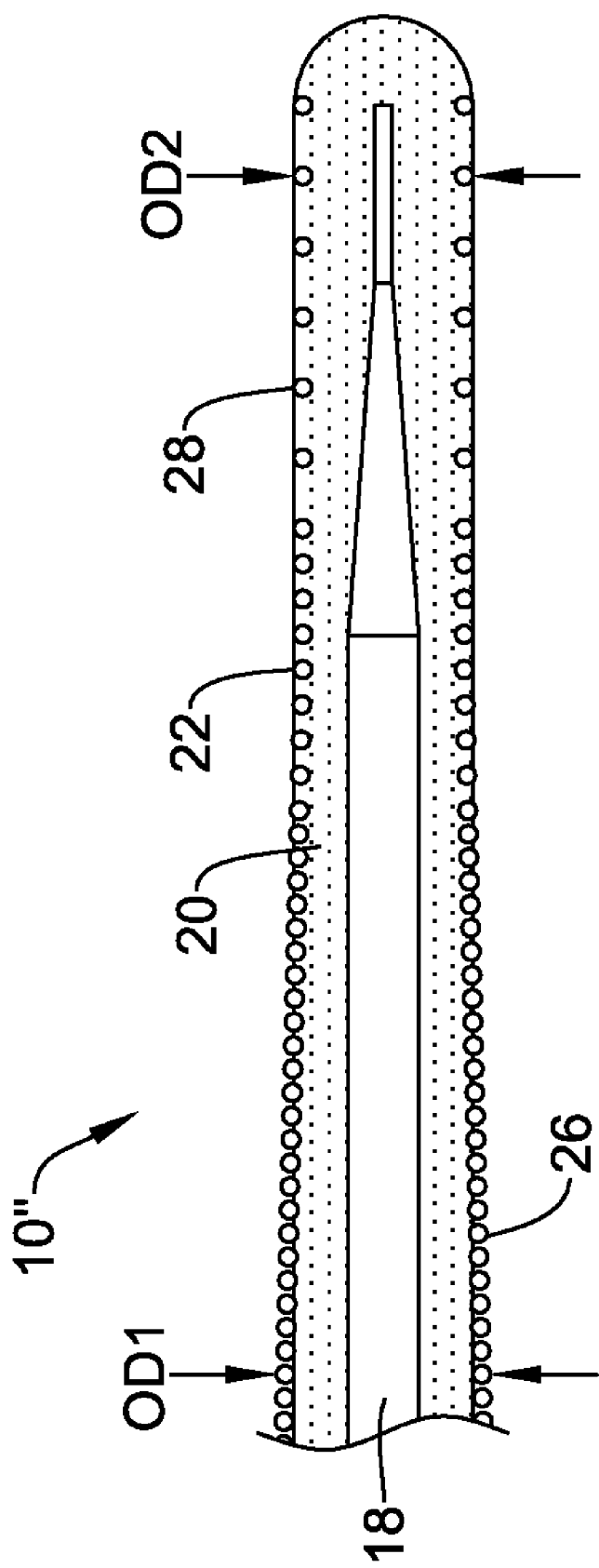
FIG. 3A is a partial cross-sectional view of another example medical device.

In addition, the pitch of coil 22 may also vary. For example, FIG. 3A illustrates guidewire 10', where first section 26 of coil 22 has a first pitch and second section 28 of coil 22 has a second pitch that is different from the first pitch. In some embodiments, the first pitch may be wound tighter than the second pitch, as shown. The reverse arrangement is also contemplated. Furthermore, coil 22 is illustrated such that outer diameter OD1 is larger than outer diameter OD2. This, however, is not intended to be limiting as changes in pitch are also contemplated in guidewires where outer diameter OD1 is smaller than outer diameter OD2 (e.g., like coil 22 in FIG. 2).

The transition between the changes in coil 22 pitch may also vary. In some embodiments, the transition from the first pitch to the second pitch may be gradual. In other embodiments, the transition may be more abrupt or stepped. Any other suitable transition may also be utilized. Moreover, coil 22 may also include one or more additional sections having a different pitch. These sections may be arranged in essentially any suitable manner and the transitions between these sections may be gradual, abrupt, stepped, etc.

Figure 7:
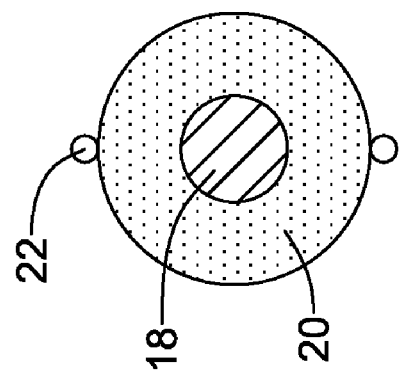
FIG. 7 is an alternative cross-sectional view.
Figure 6:
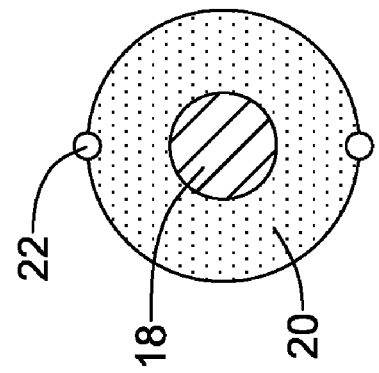
FIG. 6 is an alternative cross-sectional view.
Figure 5:
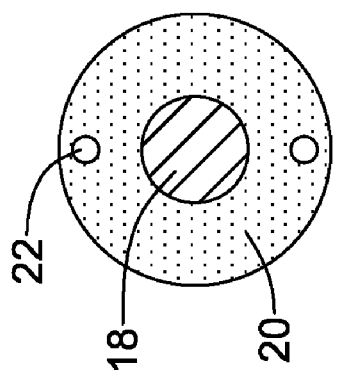
FIG. 5 is an alternative cross-sectional view.
Figure 4:
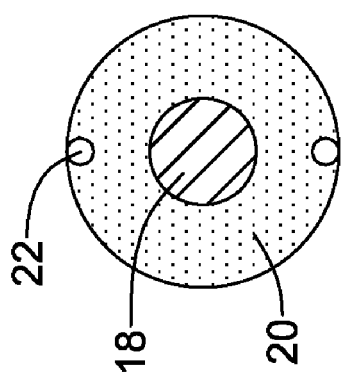
FIG. 4 is a cross-sectional view taken through line 4-4 in FIG. 2.

As illustrated in FIG. 2, second section 28 may be disposed on jacket 20 (i.e., along the outer surface of jacket 20). At least a portion of first section 26, in contrast, may be embedded within jacket 20. The level, amount, or extent of the embedding may vary. FIGS. 4-7 illustrate example cross-sectional views of guidewire 10 that illustrate some of the levels of embedding contemplated. For example, FIG. 4 shows that coil 22 may be embedded in jacket 18 such that the outer surface of coil 22 is substantially flush or even with the outer surface of jacket 20. FIG. 5 illustrates that the outer surface of coil 22 may be disposed below or axially underneath the outer surface of jacket 18. FIG. 6 illustrates that the outer surface of coil 22 may be above the outer surface of jacket 18. In this embodiment, a portion of coil 22 may protrude out from the outer surface of jacket 18. Finally, FIG. 7 illustrates that the inner surface of coil 22 may be flush or even with the outer surface of jacket 20. This last embodiment does not involve any embedding of coil 22 and may reflect the relative configuration of coil 22 and jacket 20 for other sections of coil 22 that are not embedded such as second section 28. It can be appreciated that any level of embedding shown across FIGS. 4-7 or any level in-between may be utilized for any suitable portion of coil 22.

Embedding may be accomplished using essentially any suitable methodology. For example, jacket 20 may be heated and/or softened and coil 22 may be wound so that it migrates within jacket 20 to the desired extent. Alternatively, coil 22 may be wound under tension over jacket 20 and then jacket may be heated and/or softened so that coil 22 migrates within jacket 20 to the desired extend to relieve the tension. Any other suitable method may be utilized without departing from the spirit of the invention.

The arrangement of coil 22 relative to jacket 20 may also contribute to the arrangement and/or configuration of coating 24. For example, in at least some embodiments a portion of coil 22 (e.g., first section 26) is embedded within jacket 20. Another portion of coil 22 (e.g., second section 28), in contrast, may be disposed on the outer surface of jacket 20. With coil 22 and jacket 20 configured in this manner, coating 24 may be applied to guidewire 10.

In at least some embodiments, the material selected for coating 24 is chosen for its desirable lubricity. Additionally, the material selected for coating 24 may also be chosen and so that it adheres to jacket 20 but not to coil 22. Alternatively, coil 22 may lack a primer or bonding agent that might be necessary for the selected coating 24 to adhere thereto. Accordingly, the arrangement of coil 22, jacket 20, and coating 24 may be configured so that coating 24 tends to adhere to jacket 20 but not to coil 22. Consequently, regions of guidewire 10 where coil 22 is absent from an exterior surface may include coating 24 (e.g., such that coating 24 may define the exterior surface of guidewire 10) whereas regions where coil 22 is exposed at the exterior surface may be free of coating 24 (e.g., such that coil 22 may define the exterior surface of guidewire 10). Because of this, guidewire 10 may include at least a portion that is generally lubricious (e.g., due to the presence of coating 24) and a portion that may be less lubricious (e.g., due to the absence of coating 24).

Because of the arrangements of coil 22, jacket 20, and coating 24, guidewire 10 may be provided with a number of desirable features and/or characteristics. For example, coil 22 may be arranged so that it is embedded within jacket 20 at one or more locations such that one or more regions of high lubricity can be defined. These regions may be vast (i.e., they may span significant portions of guidewire 10) or they may be localized (i.e., they may define one or more local points of heightened lubricity). Analogously, portions of coil 22 that are not embedded within jacket 20 may be free of coating 24 such that one or more regions of lower lubricity can be defined. Again, these regions may be vast (i.e., they may span significant portions of guidewire 10) or they may be localized (i.e., they may define one or more local points of lowered lubricity).

Vast and/or localized regions of increased/decreased amounts of lubricity may desirably impact the ability of a clinician to utilize guidewire 10 in a medical procedure. For example, having regions of increased lubricity may improve device handling and device exchanges as well as improve steerability and improve lesion crossing capability. Conversely, regions having decreased lubricity may be desired by clinician because these regions are easier to grasp and/or hold and/or may be better suited for engaging anatomy as desired.

In addition, by selecting a desirable configuration for coil 22, jacket 20, and coating 24, guidewire 10 may have some characteristics that resemble those of a typical "polymer tip" guidewire or device yet also have characteristics that resemble those of a typical "spring tip" guidewire or device. Some clinicians may tend to prefer a "polymer tip" or a "spring tip" for any number of reasons. Guidewire 10, by virtue of having some of the characteristics of both, may be more satisfying to a larger number of clinicians.

The various components of guidewire 10 (or other guidewires or devices disclosed herein) may include a number of features, material compositions, and dimensions as well as variations on these characteristics. Below are listed some of these characteristics for illustration purposes. As will be appreciated, any values provided for dimensions herein are provided by way of example. Dimensions other than those provided below may be used without departing from the spirit of the invention.

Core member 18 may include a proximal section 32 and a distal section 34. A connector 36 may couple or otherwise attach proximal section 32 to distal section 34. Alternatively, core member 18 may be a unitary member without a connector. A shaping member (not shown) may be coupled to core member 18, for example distal section 34 of core member 18. The shaping member may be made from a relatively inelastic material so that a clinician can bend or shape the distal end of device 10 into a shape that may facilitate navigation of device 10 through the anatomy.

Core wire 18 may have a length of about 9 to about 125 inches. Distal section 34 may make up about 5 to 80 inches of that total length, the remainder being derived from proximal section 32. In addition, core wire 18 may include a number of tapers or tapered regions. The tapered regions may be formed by any one of a number of different techniques, for example, by centerless grinding methods, stamping methods, and the like. The centerless grinding technique may utilize an indexing system employing sensors (e.g., optical/reflective, magnetic) to avoid excessive grinding of the connection. In addition, the centerless grinding technique may utilize a CBN or diamond abrasive grinding wheel that is well shaped and dressed to avoid grabbing core wire 18 during the grinding process. In some embodiments, core wire 18 is centerless ground using a Royal Master HI-AC centerless grinder to define the tapered regions.

Core wire 18 can have a solid cross-section, but in some embodiments, can have a hollow cross-section. In yet other embodiments, core wire 18 can include a combination of areas having solid cross-sections and hollow cross sections. Moreover, core wire 18, or portions thereof, can be made of rounded wire, flattened ribbon, or other such structures having various cross-sectional geometries. The cross-sectional geometries along the length of core wire 18 can also be constant or can vary. For example, FIGS. 4-7 depict core wire 18 as having a round cross-sectional shape. It can be appreciated that other cross-sectional shapes or combinations of shapes may be utilized without departing from the spirit of the invention. For example, the cross-sectional shape of core wire 18 may be oval, rectangular, square, polygonal, and the like, or any suitable shape.

The materials that can be used for the various components of guidewire 10 may include those commonly associated with medical devices, or others. For example any suitable portion or all of guidewire 10 may be made from a metal, metal alloy, polymer (some examples of which are disclosed below), a metal-polymer composite, combinations thereof, and the like, or any other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS:

N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; combinations thereof, and the like; or any other suitable material.

As alluded to above, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2-0.44% strain before plastically deforming.

In some embodiments, the linear elastic and/or non-super-elastic nickel-titanium alloy is an alloy that does not show any martensite/austenite phase changes that are detectable by DSC and DMTA analysis over a large temperature range. For example, in some embodiments, there may be no martensite/austenite phase changes detectable by DSC and DMTA analysis in the range of about −60° C. to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties and has essentially no yield point.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions of guidewire 10 may also be doped with, made of, or otherwise include a radiopaque material. For example, coil 22 may include a radiopaque material. Radiopaque materials are understood to be materials capable of producing a relatively bright image on a fluoroscopy screen or another imaging technique during a medical procedure. This relatively bright image aids the user of guidewire 10 in determining its location. Some examples of radiopaque materials can include, but are not limited to, gold, platinum, palladium, tantalum, tungsten alloy, polymer material loaded with a radiopaque filler, and the like. Additionally, radiopaque marker bands and/or coils may be incorporated into the design of guidewire 10 to achieve the same result.

In some embodiments, a degree of MRI compatibility is imparted into guidewire 10. For example, to enhance compatibility with Magnetic Resonance Imaging (MRI) machines, it may be desirable to make core wire 18 or other portions of the guidewire 10 in a manner that would impart a degree of MRI compatibility. For example, core wire 18 or portions thereof may be made of a material that does not substantially distort the image and create substantial artifacts (artifacts are gaps in the image). Certain ferromagnetic materials, for example, may not be suitable because they may create artifacts in an MRI image. Core wire 18 or portions thereof may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

Referring now to core wire 18, the entire core wire 18 can be made of the same material along its length, or in some embodiments, can include portions or sections made of different materials. In some embodiments, the material used to construct core wire 18 is chosen to impart varying flexibility and stiffness characteristics to different portions of core wire 18. For example, proximal section 32 and distal section 34 of core wire 18 may be formed of different materials, for example materials having different moduli of elasticity, resulting in a difference in flexibility. In some embodiments, the material used to construct proximal section 32 can be relatively stiff for pushability and torqueability, and the material used to construct distal section 34 can be relatively flexible by comparison for better lateral trackability and steerability. For example, proximal section 32 can be formed of straightened 304v stainless steel wire or ribbon and distal section 34 can be formed of a straightened super elastic or linear elastic alloy, for example a nickel-titanium alloy wire or ribbon.

In embodiments where different portions of core wire 18 are made of different materials, the different portions can be connected using any suitable connecting techniques and/or with connector 36. For example, the different portions of core wire 18 can be connected using welding (including laser welding), soldering, brazing, adhesive, or the like, or combinations thereof. These techniques can be utilized regardless of whether or not connector 36 is utilized. Connector 36 may include any structure generally suitable for connecting portions of a guidewire. One example of a suitable structure includes a structure such as a hypotube or a coiled wire which has an inside diameter sized appropriately to receive and connect to the ends of the proximal portion and the distal portion. Essentially any suitable configuration and/or structure can be utilized for connector 36 including those connectors described in U.S. Pat. Nos. 6,918,882 and 7,071,197 and/or in U.S. Patent Pub. No. US 2006-0122537, the entire disclosures of which are herein incorporated by reference.

As alluded to above, some portions of guidewire 10 may include a polymer. For example, jacket 20 may include a polymer. In addition, coating 24 may include a polymer. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane, polypropylene (PP), polyvinylchloride (PVC), polyether-ester (for example, ARNITEL™ available from DSM Engineering Plastics), ether or ester based copolymers (for example, butylene/poly (alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6% LCP.

Coating 24 may comprise a lubricious, hydrophilic, protective, or other type of coating. Hydrophobic coatings such as fluoropolymers provide a dry lubricity which improves guidewire handling and device exchanges. Lubricious coatings improve steerability and improve lesion crossing capability. Suitable lubricious polymers are well known in the art and may include silicone and the like, polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, the entire disclosures of which are incorporated herein by reference.

Coating 24 may be formed, for example, by coating, extrusion, co-extrusion, interrupted layer co-extrusion (ILC), or fusing several segments end-to-end. The layer may have a uniform stiffness or a gradual reduction in stiffness from the proximal end to the distal end thereof. The gradual reduction in stiffness may be continuous as by ILC or may be stepped as by fusing together separate extruded tubular segments. The outer layer may be impregnated with a radiopaque filler material to facilitate radiographic visualization. Those skilled in the art will recognize that these materials can vary widely without deviating from the scope of the present invention.

Figure 8:
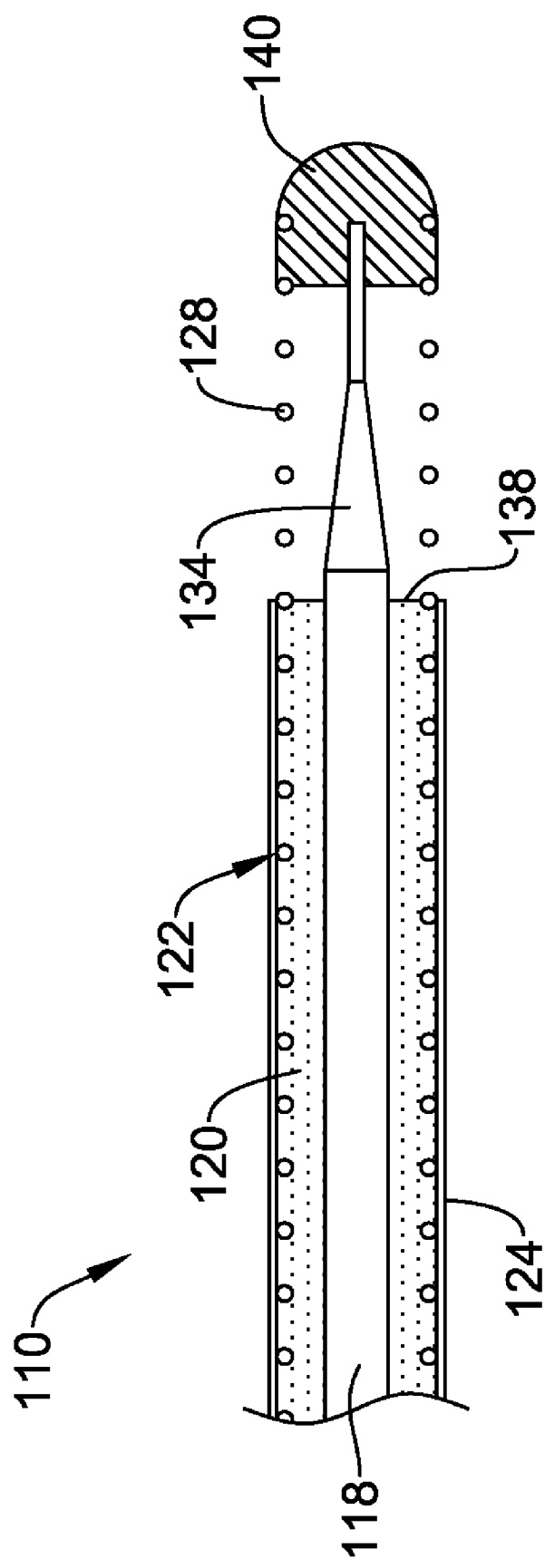
FIG. 8 is a partial cross-sectional view of another example medical device.

Turning now to FIG. 8, here another example guidewire 110 is illustrated that may be similar in form and function to any of the other guidewire disclosed herein. Guidewire 110 may include core member 118, jacket 120, and coil 122. A distal portion 128 of coil 122 may extend distally beyond the distal end 138 of jacket 120. Similarly, a distal portion 134 of core member 118 may extend beyond the distal end 138 of jacket 120. A tip member 140 may be coupled to distal portion 128 of coil 122, distal portion 134 of core member 118, or both that may define an atraumatic distal tip of guidewire 110.

A portion of coil 122 may be embedded in jacket 120, for example, similarly to coil 22. However, because distal portion 128 of coil 122 extends from distal end 138 of jacket 120, distal portion 128 is not embedded in jacket 120. Thus, coating 124, which may be similar to coating 24, may adhere to jacket 120, but not to distal portion 128 of coil 122. Because of this, guidewire 110 may have one or more regions with increased/decreased lubricity just like guidewire 10.

In some embodiments, jacket 120 (i.e., distal end 138) may extend all the way to tip member 140 prior to the completion of manufacturing and then have a portion (e.g., the portion adjacent distal portion 128 of coil 122) removed, for example, using heat, chemicals, or any other suitable means. This strategy may be desirable because, for example, it allows for coil 122 to be positioned easily. Alternatively, jacket 120 may be applied to core member 118 so that distal end 128 terminates at the location shown in FIG. 8.

In some embodiments, a similar, but reversed configuration to that shown in FIG. 8 may be used, wherein a proximal portion of coil 122 may extend proximally beyond a proximal end of jacket 120. Similarly, a distal proximal portion of core member 118 may extend beyond the proximal end of jacket 120. Again, a tip member 140 may be utilized, and may be coupled to distal portion 128 of coil 122, distal portion 134 of core member 118, or both that may define an atraumatic distal tip of guidewire 110. In such a configuration, the distal end of the jacket 120 may abut and/or contact the proximal end of the tip member 140. Again, a portion of coil 122 may be embedded in jacket 120, for example, similarly to coil 22. However, because proximal portion of coil 122 extends from proximal end of jacket 120, a proximal portion of the coil may not be embedded in jacket 120. Thus, a coating 124, which may be similar to coating 24, may adhere to jacket 120, but not to proximal portion of coil 122. Because of this, guidewire 110 may have one or more regions with increased/decreased lubricity just like guidewire 10.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A medical device, comprising:
an elongate core member having a proximal portion and a distal portion;
a polymer jacket disposed about at least a portion of the core member, the jacket including an outer surface, the polymer jacket extending distally beyond a distal end of the core member;
a lubricious coating disposed on the outer surface of the jacket;
a coil disposed around at least a portion of the jacket, the coil disposed over the distal portion of the core member, the coil having an outer surface and an inner surface and including a first section and a second section;
wherein at least a portion of the outer surface of the coil along the first section is flush with or recessed below the outer surface of the polymer jacket; and
wherein at least a portion of the outer surface of the coil along the second section protrudes from the outer surface of the polymer jacket, is free of the coating, and defines a region of decreased lubricity; and
wherein at least a portion of the inner surface of the coil along the second section contacts the polymer jacket, and
wherein the first section of the coil has a first outer diameter, and the second section of the coil has a second outer diameter.

2. The medical device of claim 1, wherein the first outer diameter is larger than the second outer diameter.

3. The medical device of claim 1, wherein the first outer diameter is smaller than the second outer diameter.

4. The medical device of claim 1, wherein the coil includes a third section having a third outer diameter different from the first outer diameter, the second outer diameter, or both.

5. The medical device of claim 1, wherein the first section of the coil is disposed proximally of the second section of the coil.

6. The medical device of claim 1, wherein the first section of the coil is disposed distally of the second section of the coil.

7. The medical device of claim 1, wherein at least a portion of the second section of the coil is disposed on the outer surface of the jacket.

8. The medical device of claim 1, wherein at least a portion of the first section of the coil is positioned under the outer surface of the jacket.

9. The medical device of claim 1, wherein the outer surface of the coil along at least a portion of the first section is flush with the outer surface of the jacket.

10. The medical device of claim 1, wherein the first section of the coil is completely embedded within the jacket.

11. The medical device of claim 1, wherein the first section of the coil is only partially embedded within the jacket.

12. The medical device of claim 1, wherein the first section of the coil includes a first region that is completely embedded within the jacket and a second region that is only partially embedded within the jacket.

13. The medical device of claim 1, wherein the first section of the coil has a first pitch and wherein the second section of the coil has a second pitch different from the first pitch.

14. The medical device of claim 1, wherein one or more additional regions of decreased lubricity are defined along the second section of the coil.

15. A medical device, comprising:
an elongate core member having a proximal portion and a distal portion;
a polymer jacket disposed on the distal portion, the jacket including an outer surface, the polymer jacket extending distally beyond a distal end of the core member;
a coil disposed on the jacket and over the distal portion of the core member, the coil having a first section having a first outer diameter and a second section having a second outer diameter different from the first outer diameter;
wherein the first section is embedded within the jacket; and
a lubricious coating disposed on the jacket,
wherein the second section of the coil is free of the coating and defines a region of decreased lubricity; and
wherein at least a portion of the second section of the coil is disposed on the outer surface of the jacket.

16. The medical device of claim 15, wherein the first section of the coil is only partially embedded within the jacket.

17. The medical device of claim 15, wherein one or more additional regions of decreased lubricity are defined along the second section of the coil.

18. The medical device of claim 15, wherein the coil includes a third section having a third outer diameter different from the first outer diameter, the second outer diameter, or both.

19. A guidewire, comprising:
an elongate core member having a proximal portion and a distal portion;
a polymer jacket disposed on the distal portion and extending distally beyond a distal end of the core member;
a coil disposed about at least a portion of the jacket over the distal portion of the core member, the coil having an outer surface and including a first section and a second section;
wherein the outer surface of the coil along the first section is flush with or recessed below the outer surface of the polymer jacket;
wherein the outer surface of the coil along the second section protrudes from the outer surface of the polymer jacket;
a lubricous coating disposed on the jacket, wherein the coating defines one or more regions of increased lubricity;
wherein the second section of the coil is free of the coating; and
wherein one or more regions of decreased lubricity are defined along the second section of the coil, and
wherein the first section of the coil has a first outer diameter, and the second section of the coil has a second outer diameter.

* * * * *